(12) United States Patent
Chang

(10) Patent No.: US 8,151,797 B2
(45) Date of Patent: Apr. 10, 2012

(54) RESPIRATION MASK ASSEMBLY

(75) Inventor: Eric Chang, Taichung Hsein (TW)

(73) Assignee: Hsiner Company, Ltd., Taichung Hsien (TW)

( * ) Notice: Subject to any disclaimer, the term of this patent is extended or adjusted under 35 U.S.C. 154(b) by 772 days.

(21) Appl. No.: 12/261,409

(22) Filed: Oct. 30, 2008

(65) Prior Publication Data

US 2010/0108069 A1 May 6, 2010

(51) Int. Cl.
*A61M 16/06* (2006.01)
(52) U.S. Cl. .............................. 128/207.11; 128/260.24
(58) Field of Classification Search ......... 128/206.11–206.29, 207.11
See application file for complete search history.

(56) References Cited

U.S. PATENT DOCUMENTS

| | | | |
|---|---|---|---|
| 2,747,464 A * | 5/1956 | Bowerman | 359/382 |
| 4,034,426 A * | 7/1977 | Hardwick et al. | 4/564.1 |
| 4,663,931 A * | 5/1987 | Schiffers et al. | 60/784 |
| 4,944,210 A * | 7/1990 | Flock et al. | 89/1.818 |
| 5,906,199 A * | 5/1999 | Budzinski | 128/201.11 |
| 6,062,148 A * | 5/2000 | Hodge et al. | 108/147 |
| 6,119,693 A * | 9/2000 | Kwok et al. | 128/207.11 |
| 6,374,826 B1 * | 4/2002 | Gunaratnam et al. | 128/206.27 |
| 6,532,961 B1 * | 3/2003 | Kwok et al. | 128/206.21 |
| 6,557,556 B2 * | 5/2003 | Kwok et al. | 128/207.11 |
| 6,691,708 B2 * | 2/2004 | Kwok et al. | 128/207.11 |
| 7,059,326 B2 * | 6/2006 | Heidmann et al. | 128/207.11 |
| 7,234,773 B2 * | 6/2007 | Raftery et al. | 297/284.4 |
| 7,610,916 B2 * | 11/2009 | Kwok et al. | 128/207.11 |
| 2003/0062048 A1 * | 4/2003 | Gradon et al. | 128/207.11 |
| 2003/0075180 A1 * | 4/2003 | Raje et al. | 128/206.24 |
| 2003/0089373 A1 * | 5/2003 | Gradon et al. | 128/206.27 |
| 2004/0182398 A1 * | 9/2004 | Sprinkle et al. | 128/207.13 |
| 2004/0255949 A1 * | 12/2004 | Lang et al. | 128/206.21 |
| 2005/0039753 A1 * | 2/2005 | Schumacher | 128/206.27 |
| 2005/0197605 A1 * | 9/2005 | Bonutti et al. | 602/5 |
| 2006/0191538 A1 * | 8/2006 | Heidmann et al. | 128/207.11 |
| 2008/0135050 A1 * | 6/2008 | Hitchcock et al. | 128/207.11 |
| 2010/0071700 A2 * | 3/2010 | Hitchcock et al. | 128/207.11 |
| 2011/0186045 A1 * | 8/2011 | Erickson | 128/201.23 |

* cited by examiner

*Primary Examiner* — Stephen Crow
(74) *Attorney, Agent, or Firm* — Jeffrey D. Myers; Peacock Myers, P.C.

(57) ABSTRACT

A respiration mask assembly including: a mask body having a front part that defines a front opening adapted to communicate fluidly with a gas supply, and a rear part that defines a rear opening opposite to the front opening in a horizontal direction; a forehead support beam extending outwardly from and pivoted to the front part of the mask body so as to rotate relative to the mask body about a first axis transverse to the horizontal direction; and a worm pivoted to the front part of the mask body. The forehead support beam has a toothed pivot end engaging the worm such that rotation of the worm about a second axis transverse to the first axis results in rotation of the forehead support beam about the first axis.

5 Claims, 5 Drawing Sheets

RESPIRATION MASK ASSEMBLY

CROSS-REFERENCE TO RELATED APPLICATIONS

Not Applicable.

STATEMENT REGARDING FEDERALLY SPONSORED RESEARCH OR DEVELOPMENT

Not Applicable.

INCORPORATION BY REFERENCE OF MATERIAL SUBMITTED ON A COMPACT DISC

Not Applicable.

COPYRIGHTED MATERIAL

Not Applicable.

BACKGROUND OF THE INVENTION

1. Field of the Invention

The invention relates to a respiration mask assembly, more particularly to a respiration mask assembly including a mask body and a forehead support beam pivoted to the mask body.

2. Description of the Related Art

FIG. 1 illustrates a conventional pressure support respiration mask assembly that includes a mask body 101 defining a front opening 102 for communicating fluidly with a gas supply (not shown) through a conduit 2, a forehead support beam 103 extending from the mask body 101 and formed with a forehead-abutting member 104 for abutting against the forehead of the wearer, a pair of upper straps 105 connected to the forehead support beam 103, and a pair of lower straps 106 connected to the mask body 101.

The conventional pressure support respiration mask assembly is disadvantageous in that the forehead support beam 103 is integrally formed with the mask body 101 and cannot be adjusted relative to the mask body 101, which can result in wearer discomfort due to a tight fastening of one of the pairs of the upper and lower straps 105, 106 when the profile from the forehead support beam 103 to the mask body 101 does not fit the facial profile of the wearer.

SUMMARY OF THE INVENTION

Therefore, the object of the present invention is to provide a respiration mask assembly that can overcome the aforesaid drawback associated with the prior art.

According to the present invention, there is provided a respiration mask assembly that comprises: a mask body having a front part that defines a front opening adapted to communicate fluidly with a gas supply, and a rear part that defines a rear opening opposite to the front opening in a horizontal direction; a forehead support beam extending outwardly from and pivoted to the front part of the mask body so as to rotate relative to the mask body about a first axis transverse to the horizontal direction; and a worm pivoted to the front part of the mask body. The forehead support beam has a toothed pivot end engaging the worm such that rotation of the worm about a second axis transverse to the first axis results in rotation of the forehead support beam about the first axis.

BRIEF DESCRIPTION OF THE DRAWINGS

The features and advantages of the present invention will become apparent in the following detailed description of the preferred embodiment with reference to the accompanying drawings, of which.

DETAILED DESCRIPTION OF THE PREFERRED EMBODIMENT

Figure 1:
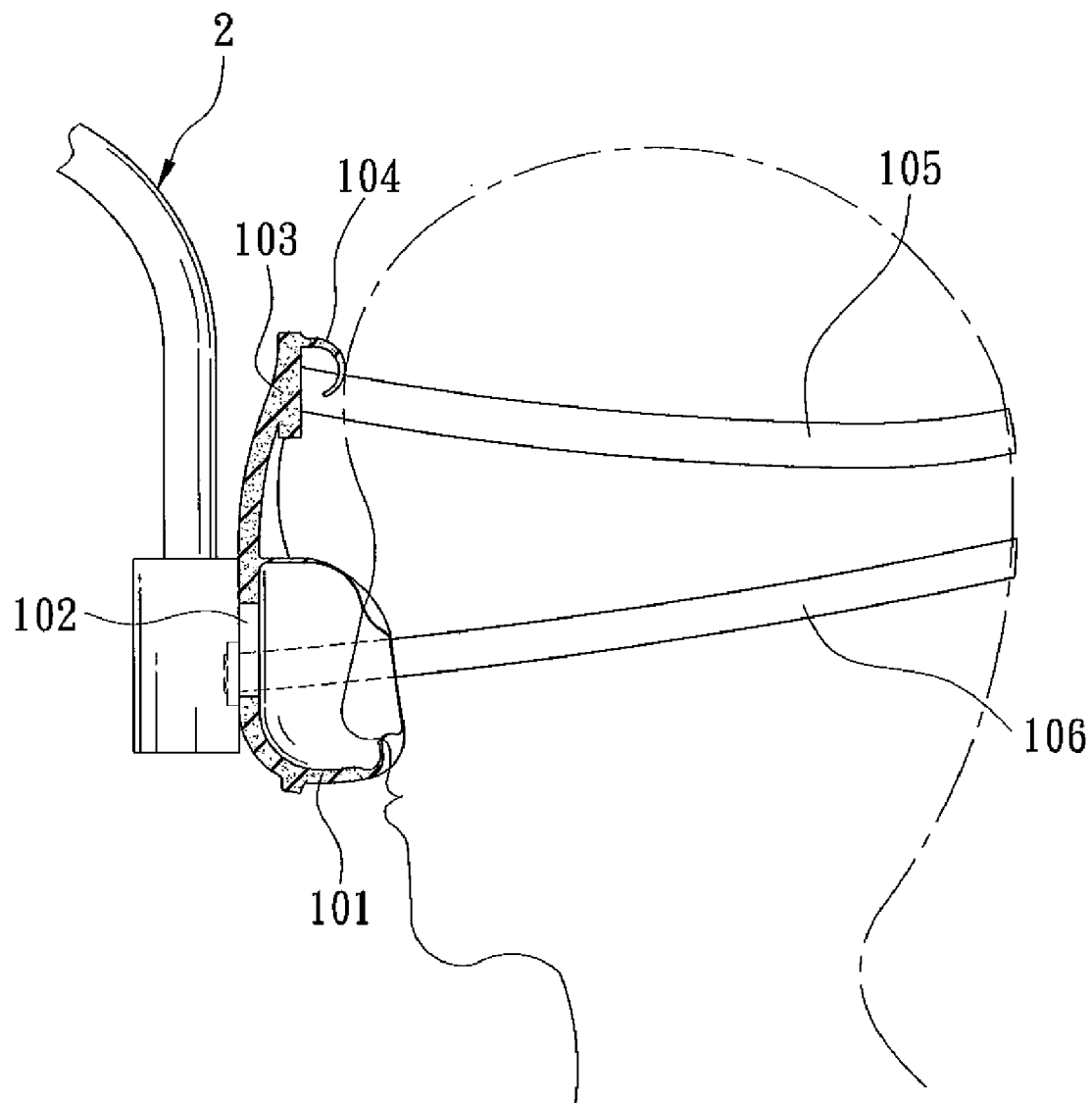
FIG. 1 is a schematic partly sectional view of a conventional pressure support respiration mask assembly.
Figure 2:
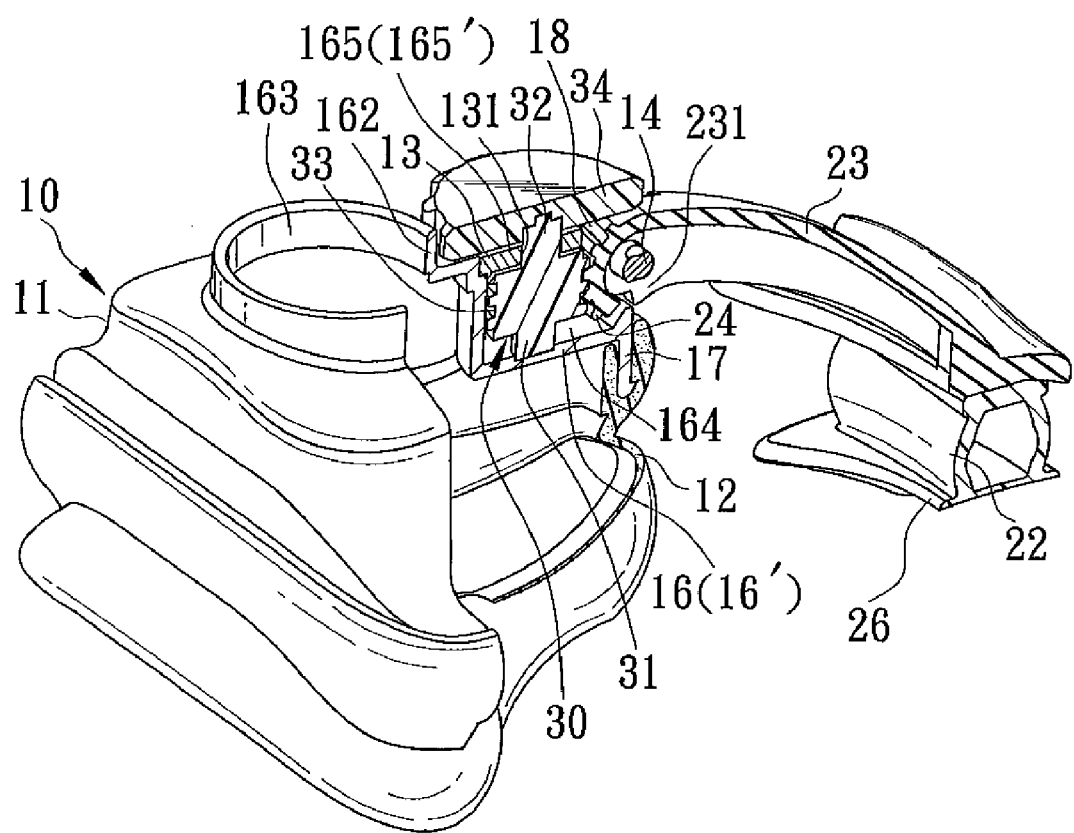
FIG. 2 is a cutaway perspective view of the preferred embodiment of a pressure support respiration mask assembly according to the present invention.
Figure 3:
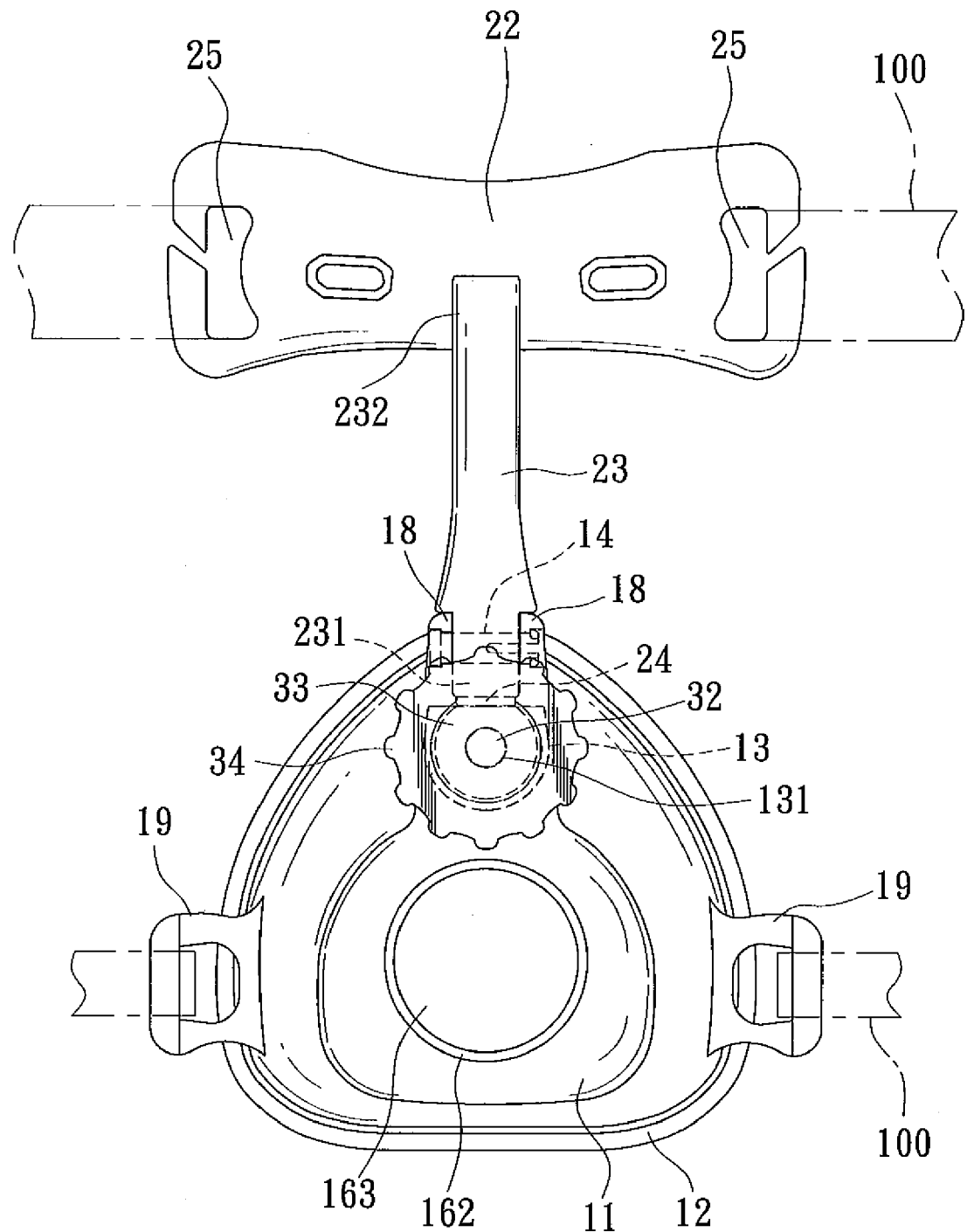
FIG. 3 is a fragmentary schematic view of the preferred embodiment.
Figure 4:
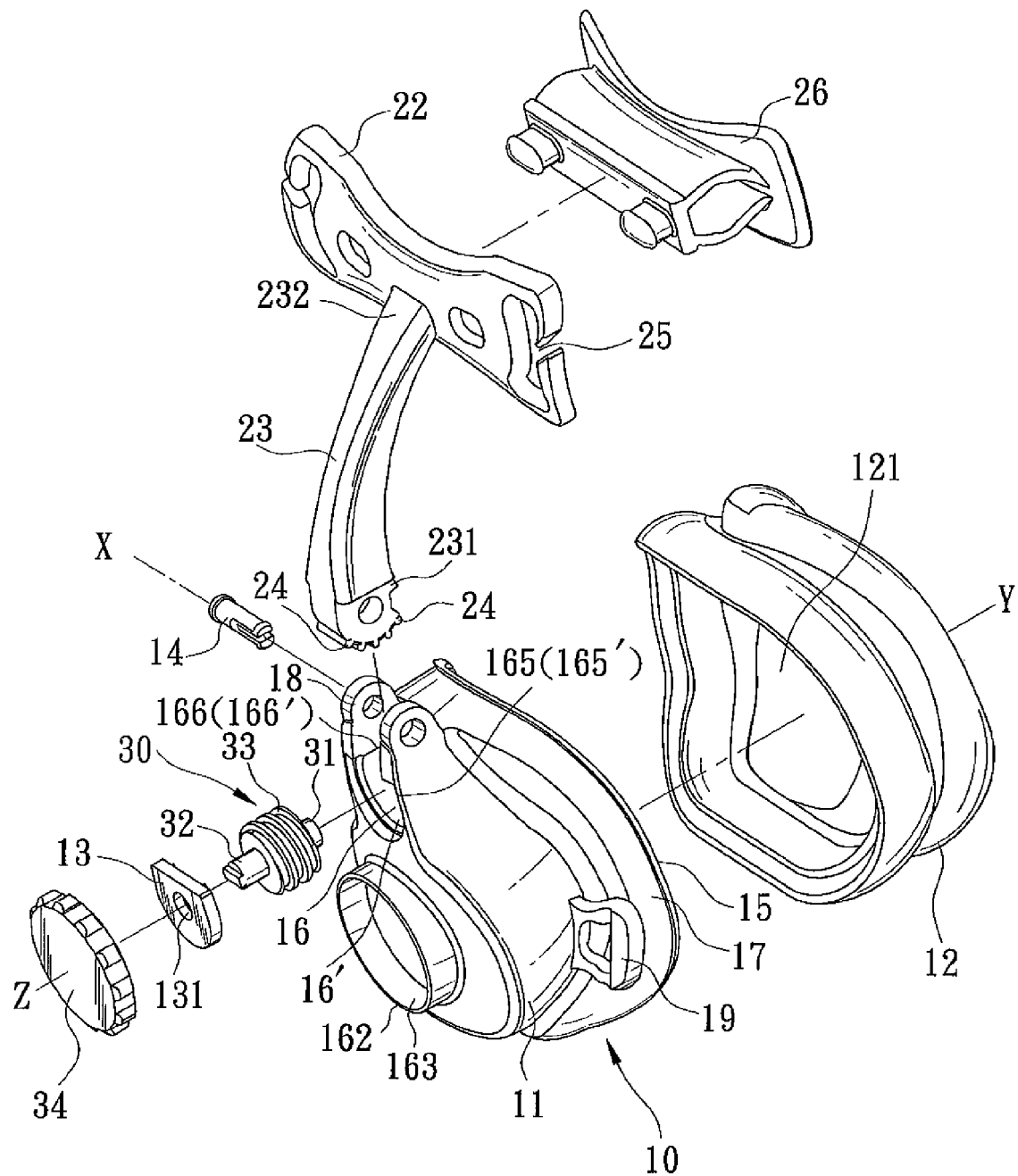
FIG. 4 is an exploded perspective view of the preferred embodiment.
Figure 5:
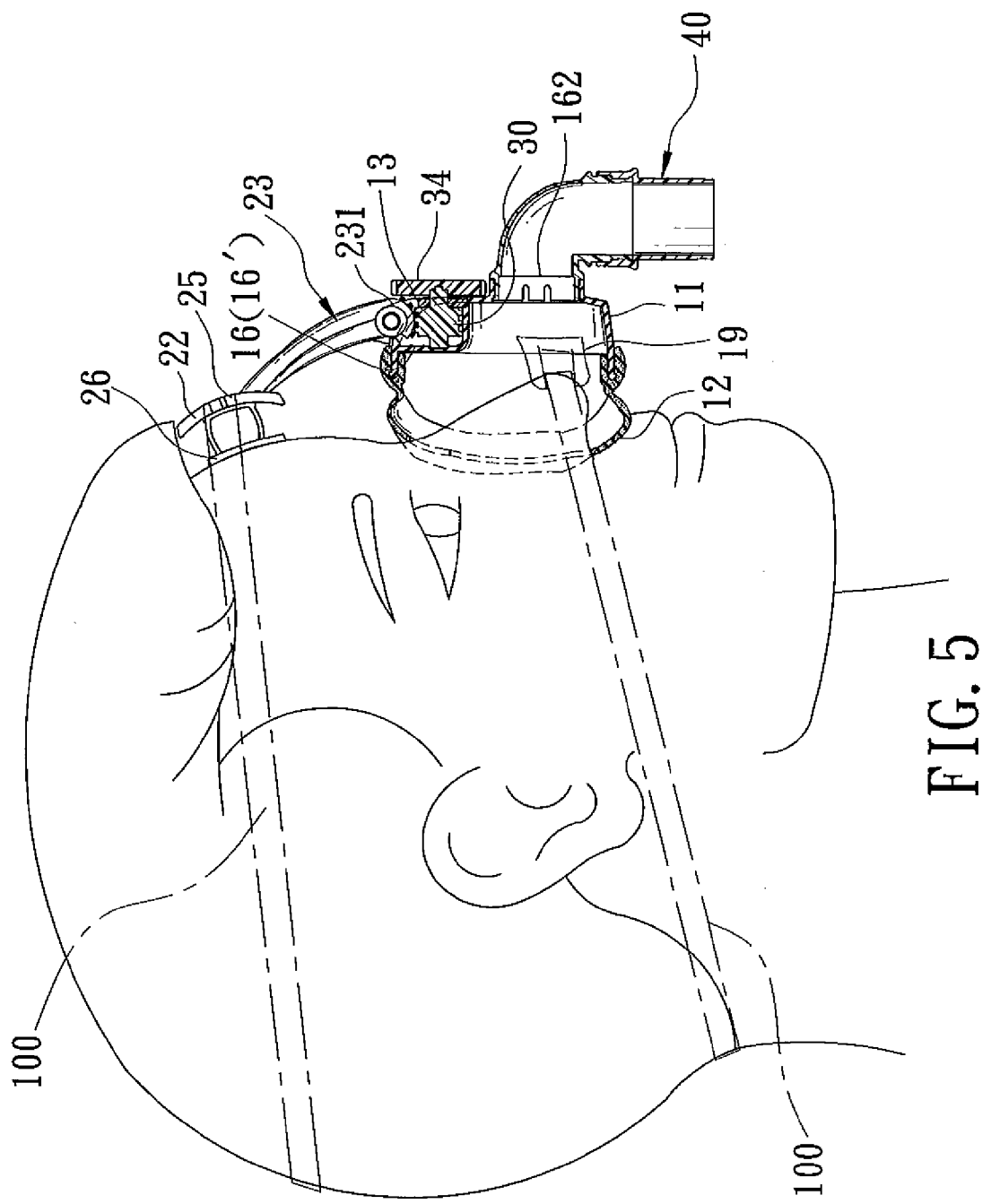
FIG. 5 is a sectional view of the preferred embodiment.

Referring to FIGS. 2-5, the preferred embodiment of a pressure support respiration mask assembly according to the present invention is shown to include: a mask body 10 having a front part 11 that defines a front opening 163 adapted to communicate fluidly with a gas supply (not shown) through a conduit 40 (see FIG. 5), and a rear part 17 that defines a rear opening 15 opposite to the front opening 163 in a horizontal direction (Y); and a forehead support beam 23 extending outwardly from and pivoted to the front part 11 of the mask body 10 so as to rotate relative to the mask body 10 about a first axis (X) transverse to the horizontal direction (Y). An annular protrusion 162 protrudes outwardly from a periphery of the front opening 163 of the front part 11 of the mask body 10 for connecting with the conduit 40.

In this embodiment, a worm 30 is pivoted to the front part 11 of the mask body 10. The forehead support beam 23 has a toothed pivot end 231 engaging the worm 30 such that rotation of the worm 30 about a second axis (Z) transverse to the first axis (X) results in rotation of the forehead support beam 23 about the first axis (X). The toothed pivot end 231 of the forehead support beam 23 has an arcuate end face formed with a plurality of teeth 24.

In this embodiment, the front part 11 of the mask body 10 is formed with a mounting recess 16. The worm 30 is received in the mounting recess 16. The mounting recess 16 is defined by a recess-defining wall 16' that has a top open end 166', a front open end 165', and a rear closed end 164 (see FIG. 2) opposite to the front open end 165' in the horizontal direction (Y). The top open end 166' defines a top opening 166 of the mounting recess 16 for extension of the toothed pivot end 231 of the forehead support beam 23 therethrough and into the mounting recess 16. The front open end 165' defines a front opening 165 of the mounting recess 16. The front part 11 of the mask body 10 is provided with a supporting plate 13 that is fitted into the front open end 165' of the recess-defining wall 16' to cover the front opening 165 of the mounting recess 16. The worm 30 has first and second pivot ends 31, 32 that are pivoted to the rear closed end 164 of the recess-defining wall 16' and the supporting plate 13, respectively, and that cooperatively define the second axis (Z). The worm 30 further has a threaded portion 33 extending between the first and second pivot ends 31, 32 and engaging the teeth 24 of the toothed pivot end 231 of the forehead support beam 23 so as to permit adjustment of the angular position of the forehead support beam 23 relative to the mask body 10. The supporting plate 13 is formed with a through-hole 131 for extension of the second pivot end 32 of the worm 30 therethrough. An operating knob 34 is disposed outwardly and frontwardly of the mounting recess 16, and is connected securely to the second pivot end 32 of the worm 30 for facilitating the operation of driving rotation of the worm 30 about the second axis (Z).

The front part 11 of the mask body 10 is further provided with a pivot shaft 14, and is further formed with two opposite pivot ears 18 protruding outwardly of the mounting recess 16 from the top open end 166' of the recess-defining wall 16'. The pivot shaft 14 defines the first axis (X), and has two opposite ends secured to the pivot ears 18, respectively. The toothed pivot end 231 of the forehead support beam 23 is disposed between the pivot ears 18 and is pivoted to the pivot shaft 14 which extends through the toothed pivot end 231 of the forehead support beam 23.

In this embodiment, a hollow cushioning member 12 is connected securely to and flares rearwardly from a periphery of the rear part 17 of the mask body 10, and has a constricted rear end that defines a constricted rear opening 121 for extension of the nose of the wearer therethrough and into the mask body 10.

In this embodiment, an elastic forehead-abutting member 26 is spaced apart from the mask body 10, and is adapted to abut against the forehead of the wearer. The forehead support beam 23 further has a connecting end 232 that is provided with an end plate 22. The forehead-abutting member 26 is mounted detachably on the end plate 22. The end plate 22 is formed with two fastening holes 25 for fastening of a pair of straps 100 to the end plate 22. The mask body 10 is further formed with two loop-shaped ears 19 for fastening of another pair of straps 100 to the mask body 10.

By pivoting the forehead support beam 23 to the front part 11 of the mask body 10 of the respiration mask assembly of this invention, the angular position of the forehead support beam 23 relative to the mask body 10 can be adjusted, thereby eliminating the aforesaid drawback associated with the prior art.

While the present invention has been described in connection with what is considered the most practical and preferred embodiment, it is understood that this invention is not limited to the disclosed embodiment but is intended to cover various arrangements included within the spirit and scope of the broadest interpretation so as to encompass all such modifications and equivalent arrangements.

What is claimed is:

1. A respiration mask assembly comprising:
a mask body having a front part that defines a front opening adapted to communicate fluidly with a gas supply, and a rear part that defines a rear opening opposite to said front opening in a horizontal direction;
a forehead support beam extending outwardly from and pivoted to said front part of said mask body so as to rotate relative to said mask body about a first axis transverse to said horizontal direction; and
a worm pivoted to said front part of said mask body, said forehead support beam having a toothed pivot end engaging said worm such that rotation of said worm about a second axis transverse to said first axis results in rotation of said forehead support beam about said first axis; and
wherein said front part of said mask body is formed with a mounting recess, said worm being received in said mounting recess; and
wherein said mounting recess is defined by a recess-defining wall that has a top open end, a front open end, and a rear closed end opposite to said front open end in the horizontal direction, said top open end defining a top opening of said mounting recess for extension of said toothed pivot end of said forehead support beam therethrough and into said mounting recess, said front open end defining a front opening of said mounting recess, said front part of said mask body being provided with a supporting plate that is fitted into said front open end of said recess-defining wall to cover said front opening of said mounting recess, said worm having first and second pivot ends that are pivoted to said rear closed end of said recess-defining wall and said supporting plate, respectively, and that cooperatively define said second axis.

2. The respiration mask assembly as claimed in claim 1, wherein said front part of said mask body is further provided with a pivot shaft, and is further formed with two opposite pivot ears protruding outwardly of said mounting recess from said top open end of said recess-defining wall, said pivot shaft defining said first axis and having two opposite ends secured to said pivot ears, respectively, said toothed pivot end of said forehead support beam being disposed between said pivot ears and being pivoted to said pivot shaft.

3. The respiration mask assembly as claimed in claim 1, further comprising an operating knob disposed outwardly and frontwardly of said mounting recess and connected securely to said second pivot end of said worm.

4. The respiration mask assembly as claimed in claim 1, further comprising a hollow cushioning member flaring rearwardly from a periphery of said rear part of said mask body and having a constricted rear end that defines a constricted rear opening for extension of the nose of the wearer therethrough and into said mask body.

5. The respiration mask assembly as claimed in claim 1, further comprising a forehead-abutting member spaced apart from said mask body and adapted to abut against the forehead of the wearer, said forehead support beam further having a connecting end that is provided with an end plate, said forehead-abutting member being mounted detachably on said end plate.

* * * * *